United States Patent [19]

Torii et al.

[11] Patent Number: 5,206,361
[45] Date of Patent: Apr. 27, 1993

[54] THIAZOLINOAZETIDINONE DERIVATIVE

[75] Inventors: Sigeru Torii, Okayama; Hideo Tanaka, Oakayama; Masatoshi Taniguchi, Tokushima; Michio Sasaoka, Tokushima; Takashi Shiroi, Tokushima; Yutaka Kameyama, Tokushima, all of Japan

[73] Assignee: Otsuka Kagaku Kabushiki Kaisha, Osaka, Japan

[21] Appl. No.: 665,863

[22] Filed: Mar. 7, 1991

[30] Foreign Application Priority Data

Mar. 8, 1990 [JP] Japan .................. 2-56956
Mar. 8, 1990 [JP] Japan .................. 2-56957

[51] Int. Cl.⁵ ............................. C07D 205/12
[52] U.S. Cl. ....................... 540/352; 540/353; 540/314
[58] Field of Search ............. 540/314, 352, 353, 310

[56] References Cited

U.S. PATENT DOCUMENTS 4,566,996 1/1986 Torii et al. .................. 540/353

Primary Examiner—Nicholas S. Rizzo
Attorney, Agent, or Firm—Armstrong, Westerman, Hattori, McLeland & Naughton

[57] ABSTRACT

The present invention provides a thiazolinoazetidinone derivative represented by the formula

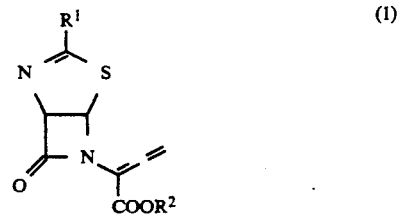

wherein $R^1$ is phenyl having or not having substituent(s), methyl having or not having substituent(s) or

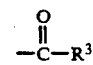

group, $R^3$ being phenyl having or not having substituent(s), and $R^2$ is a hydrogen atom or carboxylic acid protective group, and a process for preparing the same.

The present invention further provides a process for preparing a 2-exo-methylenepenam derivative characterized by hydrolyzing the thiazoline ring of a thiazolinoazetidinone derivative of the above formula (1) to effect recyclization and obtain a 2-exo-methylenepenam derivative represented by the formula

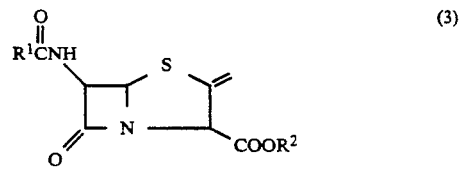

wherein $R^1$ and $R^2$ are as defined above.

1 Claim, No Drawings

THIAZOLINOAZETIDINONE DERIVATIVE

The present invention relates to novel thiazolinoazetidinone derivatives and a process for preparing 2-exo-methylenepenam derivatives therefrom.

The thiazolinoazetidinone derivative represented by the formula (1) below is useful as an intermediate for preparing β-lactam antibiotics. For example, the thiazolinoazetidinone derivative is useful as an intermediate for synthesizing 2-exo-methylenepenam derivatives represented by the formula

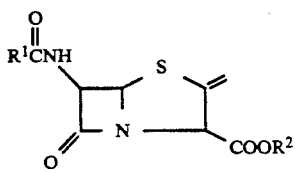
(3)

wherein $R^1$ is phenyl having or not having substituent(s), methyl having or not having substituent(s) or

group, $R^3$ being phenyl having or not having substituent(s), and $R^2$ is a hydrogen atom or a group protecting carboxylic acid (carboxylic acid protective group).

J. Chem. Soc.. Chem. Commun., 81(1987) discloses the sole process heretofore known for preparing 2-exo-methylenepenam derivatives represented by the formula (3). However, this process is low in yield, requires many cumbersome reaction or separation procedures and is in no way a satisfactory practical process.

An object of the present invention is to provide a thiazolinoazetidinone derivative which is useful as an intermediate for preparing the above 2-exo-methylenepenam derivatives in a high yield with a high purity.

A another object of the present invention is to provide a process for preparing 2-exo-methylenepenam derivatives in a high yield with a high purity, the process being free of the foregoing problems of the conventional process, safe and easy to practice and industrially advantageous.

The above and other objects of the invention will become apparent from the following description.

The present invention provides a thiazolinoazetidinone derivative represented by the formula

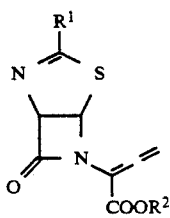
(1)

wherein $R^1$ is phenyl having or not having substituent(s), methyl having or not having substituent(s) or

group, $R^3$ being phenyl having or not having substituent(s), and $R^2$ is a hydrogen atom or carboxylic acid protective group, and a process for preparing the same.

The present invention further provides a process for preparing a 2-exo-methylenepenam derivative characterized by hydrolyzing the thiazoline ring of a thiazolinoazetidinone derivative of the above formula (1) to effect recyclization and obtain a 2-exo-methylenepenam derivative represented by the formula

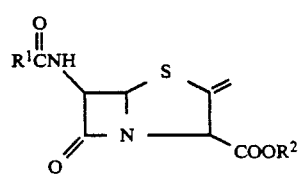
(3)

wherein $R^1$ and $R^2$ are as defined above.

The present compound of the formula (1) is novel which is not yet disclosed in literatures. The present compound can be prepared, for example, by reacting a base with a thiazolinoazetidinone derivative represented by the formula

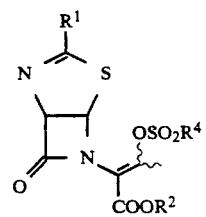
(2)

wherein $R^1$ and $R^2$ are as defined above, and $R^4$ is lower alkyl having or not having substituent(s), or phenyl having or not having substituent(s).

More specific examples of groups herein mentioned are as follows. The substituents for the phenyl group represented by $R^1$, $R^3$, or $R^4$ which may have substituent(s) include, for example, halogen atoms such as F, Cl, Br and I atoms, straight-chain or branched-chain $C_{1\sim4}$ lower alkyl groups, straight-chain or branched-chain $C_{1\sim4}$ lower alkoxy groups, straight-chain or branched-chain $C_{1\sim4}$ alkylthio groups, amino group, amino groups having one to two straight-chain or branched-chain $C_{1\sim4}$ lower alkyl groups as substituent(s), hydroxy group, protected hydroxy group, nitro group, cyano group, phenyl group,

group (wherein $R^5$ is a straight-chain or branched-chain $C_{1\sim4}$ lower alkyl group),

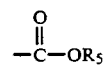

group (wherein $R^5$ is as defined above), etc. The phenyl group may have one to five such substituents which are the same or different.

Examples of methyl groups which are represented by $R^1$ and which may have substituent(s) are —$CH_3$, —$CH_2Cl$, —$CHCl_2$, —$CCl_3$, —$CH_2Br$, —$CHBr_2$, —$CBr_3$, —$CH_2F$, —$CHF_2$, —$CF_3$, —$CHXR^3$, group (wherein X is a hydrogen atom, halogen atom such as F, Cl, Br or I atom, hydroxyl group, protected hydroxyl group, acetoxy group, amino group or protected amino group, and $R^3$ is as defined above),

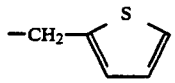

group, —$CY_2R^3$ group (wherein Y is a halogen atom such as F, Cl, Br or I atom, and $R^3$ is as defined above), —$CH_2OR^3$, group (wherein $R^3$ is as defined above), etc.

Examples of carboxylic acid protective groups represented by $R^2$ are benzyl, p-methoxybenzyl, p-nitrobenzyl, diphenylmethyl, trichloroethyl, methyl, ethyl and tert-butyl groups, and groups disclosed in Theodora W. Greene, "Protective Groups in Organic Synthesis," Chap. 5 (pp.152~192).

Examples of lower alkyl groups which are represented by $R^4$ and which may have substituent(s) are methyl, ethyl, propyl, i-propyl, butyl, i-butyl, tert-butyl, —$CH_2Cl$. —$CHCl_2$, —$CCl_3$, —$CH_2Br$, —$CHBr_2$, —$CBr_3$, —$CH_2F$, —$CHF_2$, —$CF_3$, —$CH_2CH_2F$, —$CH_2CH_2Cl$, —$CH_2CH_2Br$, —$CH_2CHF_2$, —$CH_2CHCl_2$, —$CH_2CHBr_2$, —$CH_2CF_3$, —$CH_2CCl_3$, —$CH_2CBr_3$, etc.

Examples of protective groups for the protected hydroxyl group herein mentioned as substituent(s) for some groups are those disclosed in Theodora W. Greene, "Protective Groups in Organic synthesis," Chap.2 (pp.10~72).

Examples of protective groups for the protected amino group herein given as substituent(s) for the group mentioned are those disclosed in Theodora W. Greene, "Protective Groups in Organic Synthesis," Chap.7 (pp.218~287).

The starting compound of the formula (2) is prepared, for example, by the process disclosed in JP-A-105051/1976, Reference Example 32 or 33. In order to obtain the present compound, the above compound of the formula (2) is reacted with a base in an appropriate solvent. The base to be used is preferably an aliphatic or aromatic amine. Examples of useful amines are triethylamine, diisopropylamine, ethyldiisopropylamine, tributylamine, DBN(1,5-diazabicyclo[3.4.0]nonene-5), DBU(1,5-diazabicyclo[5.4.0]undecene-5), DABCO(1,4-diazabicyclo[2.2.2]octane), piperidine, N-methylpiperidine. 2,2,6,6-tetramethylpiperidine. morpholine, N-methylmorpholine, N,N-dimethylaniline, N,N-dimethylaminopyridine and the like. These bases are used in an amount usually of 1 to 12 moles, preferably of 1 to 6 moles, per mole of the compound of the formula (2). A wide variety of solvents are usable insofar as they dissolve the compound of the formula (2) and remain inert under the reaction conditions. Examples of useful solvents are lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ethers such as diethyl ether, ethyl propyl ether, ethyl butyl ether, dipropyl ether. diisopropyl ether, dibutyl ether, methyl cellosolve and dimethoxyethane; cyclic ethers such as tetrahydrofuran and dioxane; nitriles such as acetonitrile, propionitrile, butyronitrile, isobutyronitrile and valeronitrile; substituted or unsubstituted aromatic hydrocarbons such as benzene, toluene, xylene, chlorobenzene and anisole; hydrocarbon halides such as dichloromethane, chloroform, dichloroethane, trichloroethane, dibromoethane, propylene dichloride, carbon tetrachloride and Freons; hydrocarbons such as pentane, hexane, heptane and octane; cycloalkanes such as cyclopentane, cyclohexane, cycloheptane and cyclooctane; amides such as dimethylformamide and dimethylacetamide; dimethyl sulfoxide etc. These solvents are used singly, or at least two of them are used in mixture. Further these solvents may contain water when so required. The solvent is used in an amount of about 0.5 to about 200 liters, preferably about 1 to about 50 liters, per kilogram of the compound of the formula (2). The reaction is conducted at a temperature of −70° C. to 50° C., preferably −50° C. to 0° C. After completion of the reaction, the present compound is subjected, for example, to an extraction step and/or recrystallization step in the usual manner, whereby the desired present compound can be obtained in the form of a substantially pure product, while some other purification method can of course be employed.

According to the present invention, the thiazoline ring of the thiazolinoazetidinone derivative represented by the formula (1) is hydrolyzed to obtain a 2-exo-methylenepenam derivative through recyclization. The compound of the formula (1) is prepared, for example, by reacting a compound of the formula (2) with a base. In the present invention, the compound of the formula (1) prepared from the compound of the formula (2) is usable also as it is without being isolated to hydrolyze the thiazoline ring of the compound of the formula (1) to obtain the desired 2-exo-methylenepenam derivative through recyclization.

According to the present invention, the compound of the formula (1) prepared from the compound of the formula (2) is subjected to the reaction preferably in a suitable solvent regardless of whether the compound (1) is reacted as prepared or as isolated.

To hydrolyze the thiazoline ring of the thiazolinoazetidinone derivative represented by the formula (1) to obtain the desired 2-exo-methylenepenam derivative (3) through recyclization, the compound of the formula (1) is reacted with water in the presence of an acid. The acid to be used is not limited specifically but can be any of wide varieties of known inorganic acids and organic acids, such as hydrochloric acid, sulfuric acid, nitric acid, perchloric acid, phosphoric acid, methanesulfonic acid, benzenesulfonic acid, benzenesulfonic acid substituted with one to five halogen atoms such as F, Cl, Br and I atoms, toluenesulfonic acid, trifluoromethanesulfonic acid, camphersulfonic acid, formic acid, acetic acid, monochloroacetic acid, dichloroacetic acid, trichloroacetic acid, monofluoroacetic acid, difluoroacetic acid, trifluoroacetic acid, benzoic acid and benzoic acid substituted with one to five halogen atoms such as F, Cl, Br and I atoms. In the case where the compound of the formula (1) prepared from the compound of the formula (2) is to be reacted as it is without isolation, the salt formed by the base used and the above-mentioned acid to be used is also usable as an acid according to the invention. The acid, which is used theoretically in a catalytic amount, is used generally in an amount of 0.01 to 50 moles, preferably 0.1 to 30 moles, per mole of the compound represented by the formula (1).

The water for use in the hydrolysis of the thiazoline ring, which may be used theoretically in an amount of one mole per mole of the compound of the formula (1), is used usually in an amount of 1 to 1500 moles, preferably 1 to 1000 moles, per mole of the compound. When the acid to be used is in the form of an aqueous solution or has crystal water, water need not always be additionally used.

The reaction for hydrolyzing the thiazoline ring to obtain the desired 2-exo-methylenepenam derivatives by recyclization is conducted at a temperature of −70° C. to 50° C., preferably −50° C. to 10° C.

The mixture obtained om completion of the reaction is subjected, for example, to an extraction step in the usual manner, whereby the desired 2-exo-methylenepenam derivative of the formula (3) can be obtained in the form of a substantially pure product, while some other purification method can of course be employed.

The desired 2-exo-methylenepenam derivative represented by the formula (3) can be prepared from a novel thiazolinoazetidinone derivative of the formula (1) in a high yield and with a high purity by the process of the invention which is easy to practice and industrially advantageous.

The present invention will be described in greater detail with reference to the following examples, in which "Ph" stands for phenyl.

EXAMPLE 1

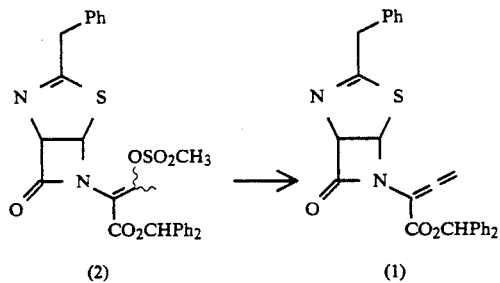

A 50 mg quantity of a compound (2) ($R^1$=benzyl, $R^2$=diphenylmethyl, $R^3$=methyl) was dissolved in N,N-dimethylformamide (1 ml), and the solution was cooled to −20° C. With addition of triethylamine (0.03 ml), the solution was reacted at −20° C. for 2 hours with stirring. The mixture was thereafter subjected to extraction with ethyl acetate. The extract was thereafter concentrated at a reduced pressure, giving a compound (1) ($R^1$=benzyl, $R^2$=diphenylmethyl).

NMR(CDCl$_3$) ; δ ppm
3.64. 3.76(ABq, 2H, J=16Hz), 5.54, 5.62(ABq, 2H, J=16Hz),
5.82(d, 1H, J=4Hz), 5.87(d, 1H, J=4Hz), 6.68(s, 1H), 7.05~7.20(m, 15H)

EXAMPLE 2

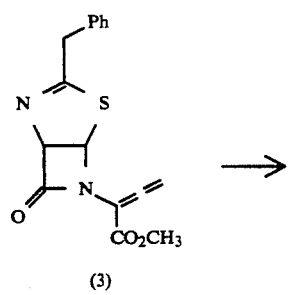

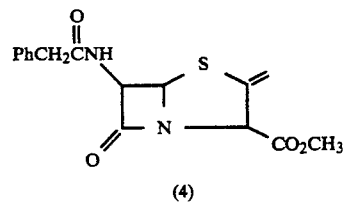

A 170 mg quantity of a compound (3) ($R^1$=benzyl, $R^2$=methyl) was dissolved in N,N-dimethylformamide (1 ml), and the solution was cooled to −10° C. With addition of 0.2 ml of 5% dilute hydrochloric acid, the solution was reacted at −10° C. for 5 minutes with stirring. The reaction mixture was then subjected to extraction with ethyl acetate. The organic layer was washed with saturated saline, dried over anhydrous MgSO$_4$ and thereafter concentrated at a reduced pressure. The resulting residue was purified by silica gel column chromatography, giving a compound (4) ($R^1$=benzyl, $R^2$=methyl) in a yield of 85% .

NMR(CDCl$_3$) ; δ ppm
3.62(ABq, 2H, J=16Hz), 3.78(s, 3H), 5.19(t, 1H, J=2Hz),
5.28(t, 1H, J=2Hz), 5.40(t, 1H, J=2Hz), 5.60(d, 1H, J=4Hz),
5.77(dd, 1H, J=4Hz and 9Hz), 6.20(d, 1H, 9Hz), 7.27~7.39(m, 5H)

EXAMPLE 3

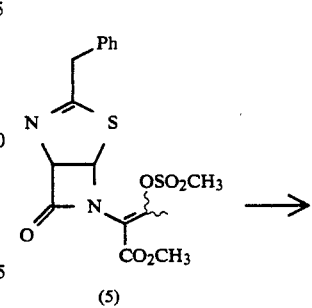

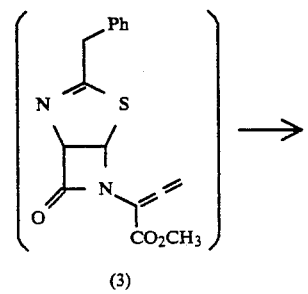

-continued (structure 4): PhCH2C(=O)NH- attached to azetidinone fused with S-containing ring bearing =CH2 and CO2CH3 group (4)

A 704 mg quantity of a compound (5) ($R^1$=benzyl, $R^2$=methyl, $R^3$=methyl) was dissolved in N,N-dimethylformamide (5 ml), and the solution was cooled to −20° C. With addition of triethylamine (1 ml), the solution was reacted at −20° C. for one hour with stirring. To the reaction mixture was added 5% dilute hydrochloric acid (10 ml), followed by extraction with ethyl acetate. The organic layer was washed with saturated saline, dried over anhydrous MgSO4 and thereafter concentrated at a reduced pressure. The resulting residue was purified by silica gel column chromatography, giving a compound (4) ($R^1$=benzyl, $R^2$=methyl) in a yield of 80%.

EXAMPLE 4

A 30 mg quantity of a compound (5) ($R^1$=benzyl, $R^2$=diphenylmethyl, $R^3$=methyl) was dissolved in N,N-dimethylformamide (1 ml), and the solution was cooled to −20° C. With addition of triethylamine (18 μl), the solution was reacted at −20° C. for one hour with stirring. To the reaction mixture was added 70% perchloric acid (50 μl), and the mixture was heated to 0° C. The mixture was reacted at 020 C. for 2.5 hours with stirring, water was then added to the mixture, and the mixture was thereafter subjected to extraction with ethyl acetate. The organic layer was washed with saturated saline, dried over anhydrous MgSO4 and thereafter concentrated at a reduced pressure. The crystals separating out were filtered off with use of ether, giving a compound (4) ($R^1$=benzyl, $R^2$=diphenylmethyl) in a yield of 82%.

NMR(CDCl3) ; δ ppm
3.62(s, 2H), 5.26~5.28(m, 2H), 5.37(t, 1H, J=2Hz), 5.61(d, 1H, J=4Hz), 5.76(dd, 1H, J=4Hz and 9Hz), 6.14(d, 1H, J=9Hz), 6.82(s, 1H), 7.20~7.41(m, 15H)

EXAMPLE 5

A compound (5) ($R^1$=benzyl, $R^2$=p-methoxybenzyl, $R^3$=methyl) was reacted in the same manner as in Example 3 to obtain a compound (4) ($R^1$=benzyl, $R^2$=p-methoxybenzyl).

EXAMPLE 6

A compound (5) ($R^1$=phenoxymethyl, $R^2$=p-nitrobenzyl, $R^3$=methyl) was reacted in the same manner as in Example 3 to obtain a compound (4) ($R^1$=phenoxymethyl, $R^2$=nitrobenzyl).

EXAMPLE 7

A compound (5) ($R^1$=benzyl, $R^2$=diphenylmethyl, $R^3$=methyl) was reacted in the same manner as in Example 3 to obtain a compound (4) ($R^1$=benzyl, $R^2$=diphenylmethyl).

We claim:
1. A thiazolinoazetidinone derivative represented by the formula

(1)

wherein $R^1$ is selected from the group consisting of phenyl, substituted phenyl, methyl, substituted methyl and $$-\overset{O}{\underset{\|}{C}}-R^3$$

group, $R^3$ being one of phenyl and substituted phenyl, and $R^2$ being one of a hydrogen atom and a carboxylic acid protective group, wherein substituents of the substituted phenyl are selected from the group consisting of halogen atoms, straight-chain or branched-chain $C_{1-4}$ lower alkyl groups, straight-chain or branched-chain $C_{1-4}$ lower alkoxy groups, straight-chain or branched-chain $C_{1-4}$ alkylthio groups, amino group, amino groups having one to two straight-chain or branched-chain $C_{1-4}$ lower alkyl groups as substituent(s), hydroxy group, protected hydroxy group, nitro group, cyano group, phenyl group $$-\overset{O}{\underset{\|}{C}}-R^5$$

group (wherein $R^5$ is a straight-chain or branched-chain $C_{1-4}$ lower alkyl group), and $$-\overset{O}{\underset{\|}{C}}-OR_5$$

group (wherein $R^5$ is as defined above); and
said substituted methyl is selected from the group consisting of —CH2Cl, —CHCl2, —CCl3, —CH2Br, —CHBr2, —CBr3, —CH2F, —CHF2, —CF3, —CHX$R^3$ group (wherein X is a hydrogen atom, a halogen atom, hydroxyl group, protected hydroxyl group, acetoxy group, amino group or protected amino group, and $R^3$ is as defined above), —CH2-(thienyl) group, —CY2$R^3$ group (wherein Y is a halogen atom and $R^3$ is as defined above), and —CH2O$R^3$ group (wherein $R^3$ is as defined above).

* * * * *